(12) United States Patent
Farin et al.

(10) Patent No.: US 10,314,612 B2
(45) Date of Patent: Jun. 11, 2019

(54) SURGICAL TOOL INTRODUCER

(71) Applicant: EON Surgical LTD., Tel-Aviv (IL)

(72) Inventors: Danny Farin, Hod-Ha'Sharon (IL); Yehuda Bachar, Givat-Shmuel (IL)

(73) Assignee: EON SURGICAL LTD., Tel-Aviv (IL)

( * ) Notice: Subject to any disclaimer, the term of this patent is extended or adjusted under 35 U.S.C. 154(b) by 0 days.

(21) Appl. No.: 15/611,374

(22) Filed: Jun. 1, 2017

(65) Prior Publication Data
US 2017/0265889 A1 Sep. 21, 2017

Related U.S. Application Data

(62) Division of application No. 14/188,095, filed on Feb. 24, 2014, now Pat. No. 9,693,798.

(60) Provisional application No. 61/768,846, filed on Feb. 25, 2013.

(51) Int. Cl.
A61B 17/00 (2006.01)
A61B 17/29 (2006.01)
A61B 17/34 (2006.01)
A61B 90/00 (2016.01)
A61B 90/30 (2016.01)

(52) U.S. Cl.
CPC ............. *A61B 17/34* (2013.01); *A61B 17/29* (2013.01); *A61B 2017/00017* (2013.01); *A61B 2017/00398* (2013.01); *A61B 2017/00473* (2013.01); *A61B 2017/00734* (2013.01); *A61B 2017/294* (2013.01); *A61B 2017/2931* (2013.01); *A61B 2017/2946* (2013.01); *A61B 2090/309* (2016.02); *A61B 2090/3614* (2016.02)

(58) Field of Classification Search
CPC ......... A61B 17/00; A61B 19/00; A61B 17/34; A61B 1/04; A61B 1/32
USPC ...................... 606/1, 108, 227; 600/190, 208
See application file for complete search history.

(56) References Cited

U.S. PATENT DOCUMENTS 5,071,430 A * 12/1991 de Salis ........... A61B 17/07207
227/155
5,336,238 A 8/1994 Holmes et al.
5,352,219 A 10/1994 Reddy
(Continued)

FOREIGN PATENT DOCUMENTS

CN 101843518 A 9/2010
CN 102228389 A 11/2011
(Continued)

*Primary Examiner* — John R Downey
(74) *Attorney, Agent, or Firm* — Baker and Hostetler LLP

(57) ABSTRACT

A tool introducer is configured for introduction in an elongated body including a straight tube, wherein the tube encloses a tube lumen opened at its distal end with a tube opening. The tool introducer includes locking means to selectively lock or unlock an interchangeable surgical tool to the tube from displacing axially and/or rotationally in the tube lumen, the locking means being configured such that, at the locking, a tool connector of the tool projects towards the tube opening and is distanced therefrom by at least 3 cm. A method includes positioning the surgical tool introducer such that a distal portion thereof projects in a body cavity, manipulating and/or extending the tool introducer to reach and engage an elongated shaft introduced percutaneously into the body cavity; and inserting the elongated shaft into the tube lumen via the tube opening and connecting the tool to the elongated shaft.

20 Claims, 11 Drawing Sheets

(56) References Cited

U.S. PATENT DOCUMENTS

| | | | |
|---|---|---|---|
| 5,441,059 A | 8/1995 | Dannan | |
| 5,593,402 A | 1/1997 | Patrick | |
| 5,832,929 A | 11/1998 | Rudko et al. | |
| 5,968,066 A | 10/1999 | Fogarty et al. | |
| 6,695,772 B1* | 2/2004 | Bon | A61B 17/3421 600/114 |
| 6,723,043 B2 | 4/2004 | Kleeman et al. | |
| 7,094,200 B2 | 8/2006 | Katzman | |
| 7,666,181 B2* | 2/2010 | Abou El Kheir | A61B 17/3421 600/104 |
| 8,133,254 B2* | 3/2012 | Dumbauld | A61B 18/1445 606/205 |
| 9,211,373 B2* | 12/2015 | Dexter | A61B 17/14 |
| 2011/0208007 A1* | 8/2011 | Shohat | A61B 17/3403 600/227 |
| 2012/0259325 A1 | 10/2012 | Houser et al. | |

FOREIGN PATENT DOCUMENTS

| | | | | |
|---|---|---|---|---|
| JP | 2010-253270 A | 11/2010 | | |
| WO | 2011/089565 A1 | 7/2011 | | |
| WO | WO 2011089565 A1 * | 7/2011 | ....... | A61B 17/00234 |
| WO | 2012/035524 A2 | 3/2012 | | |

\* cited by examiner

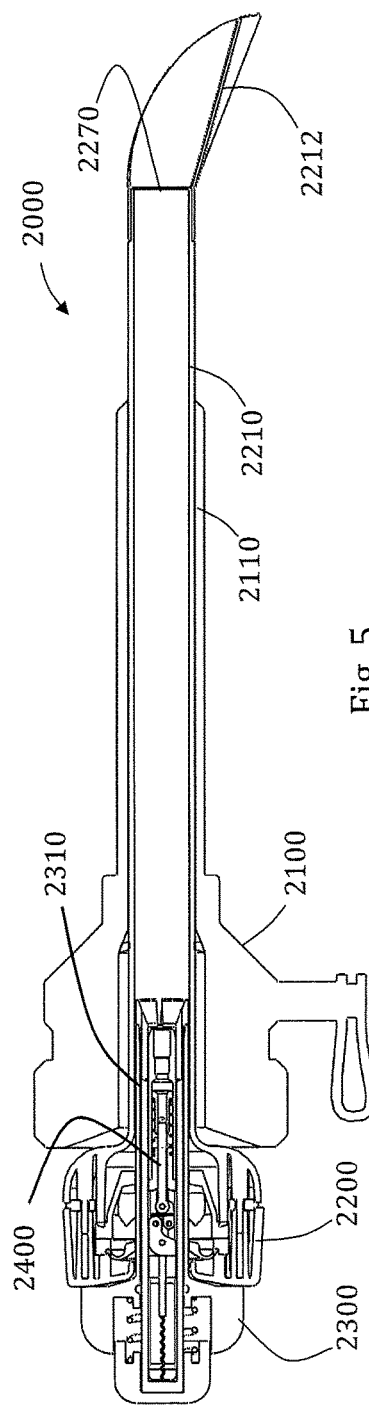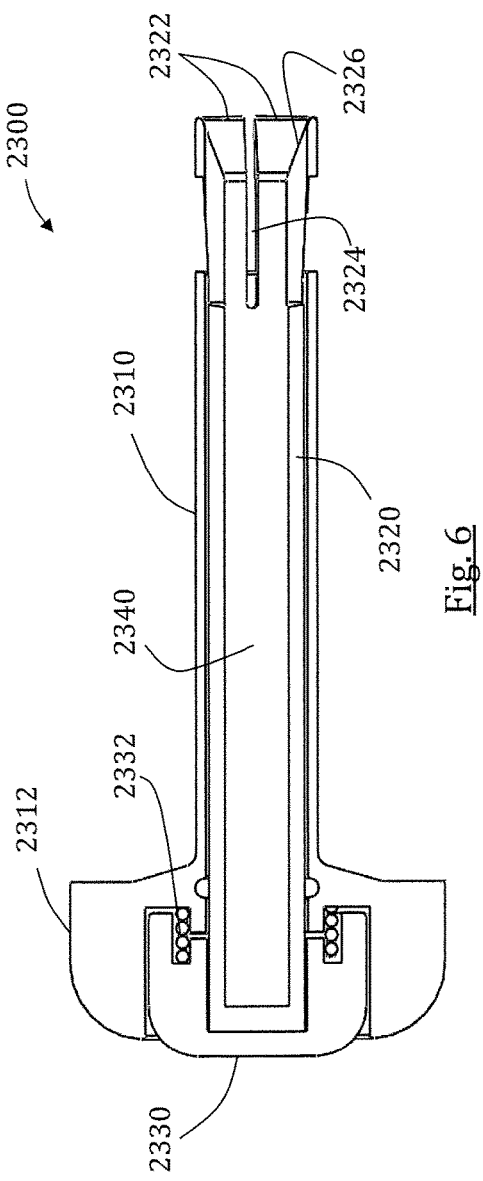

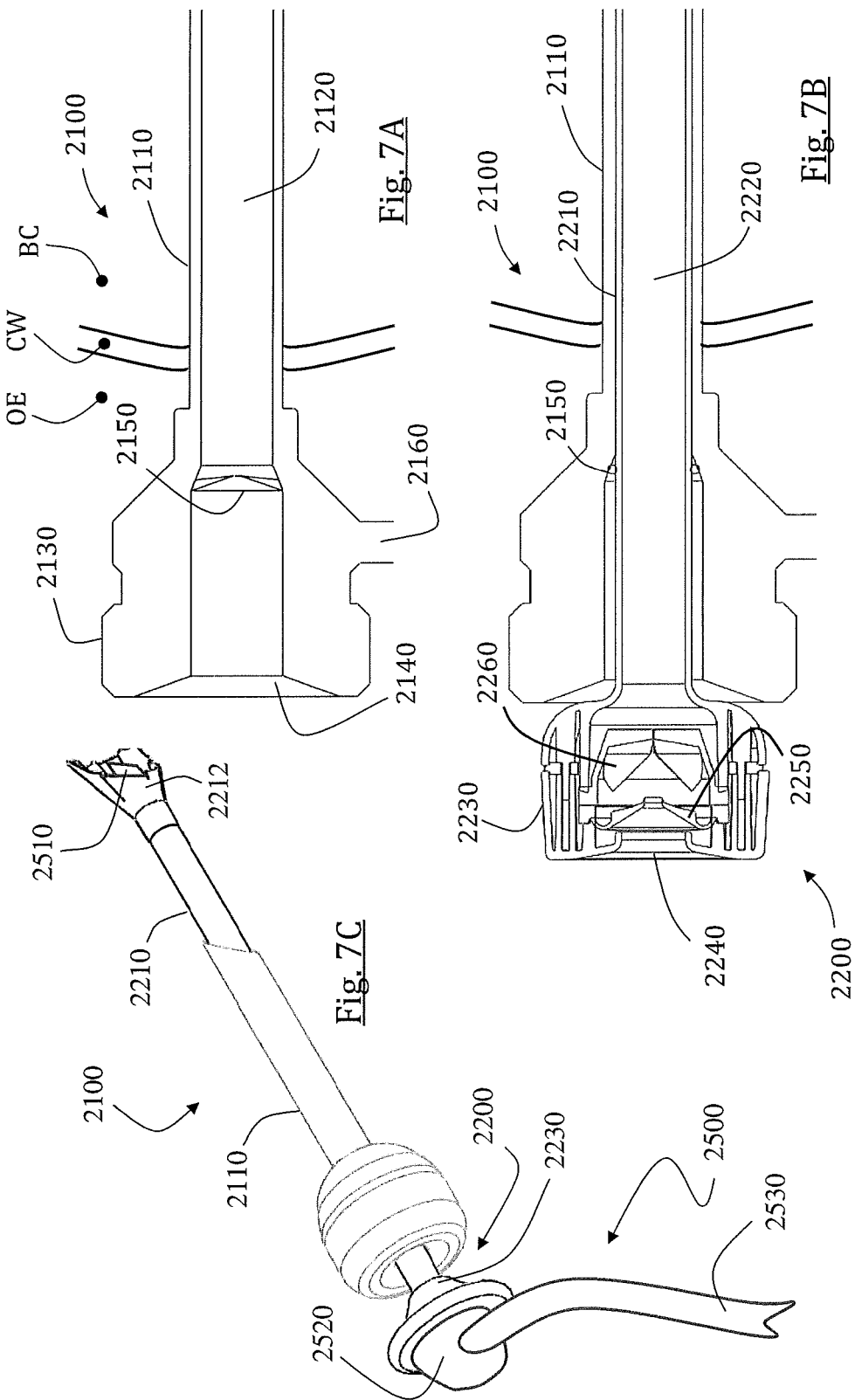

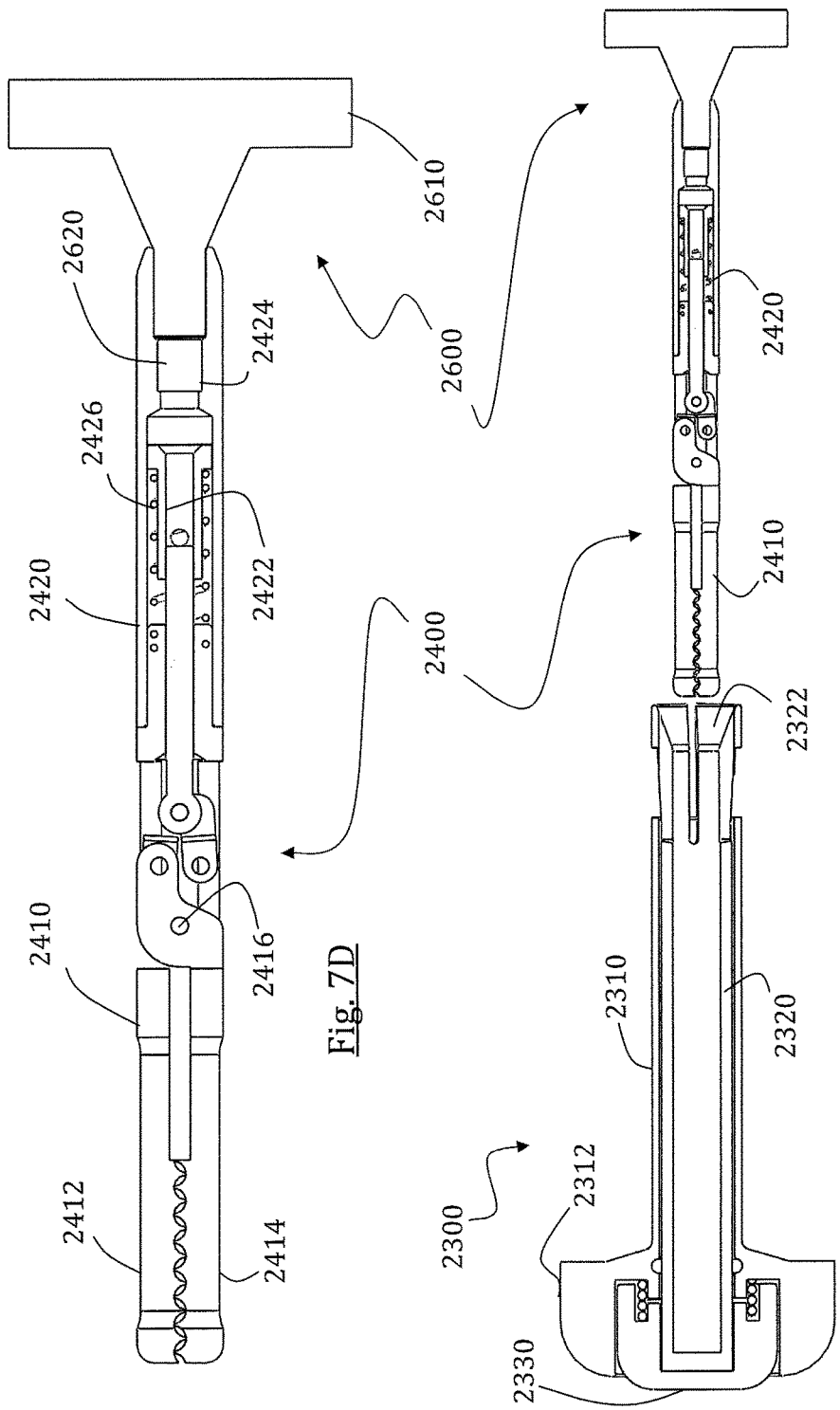

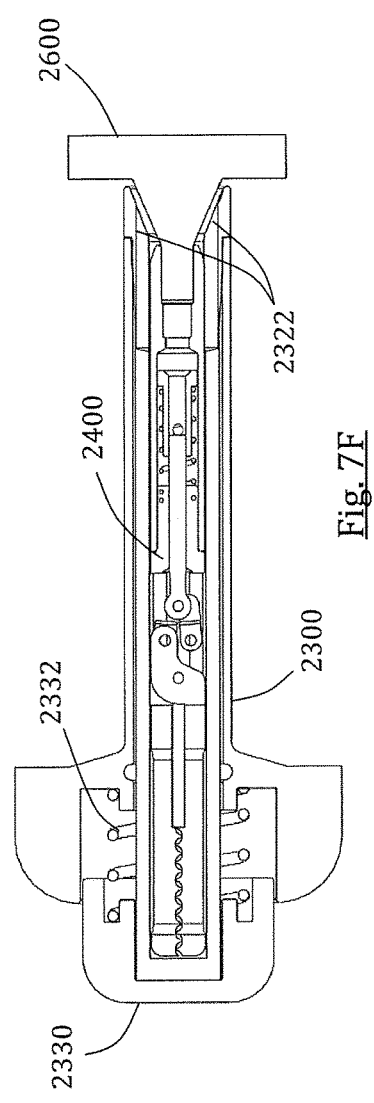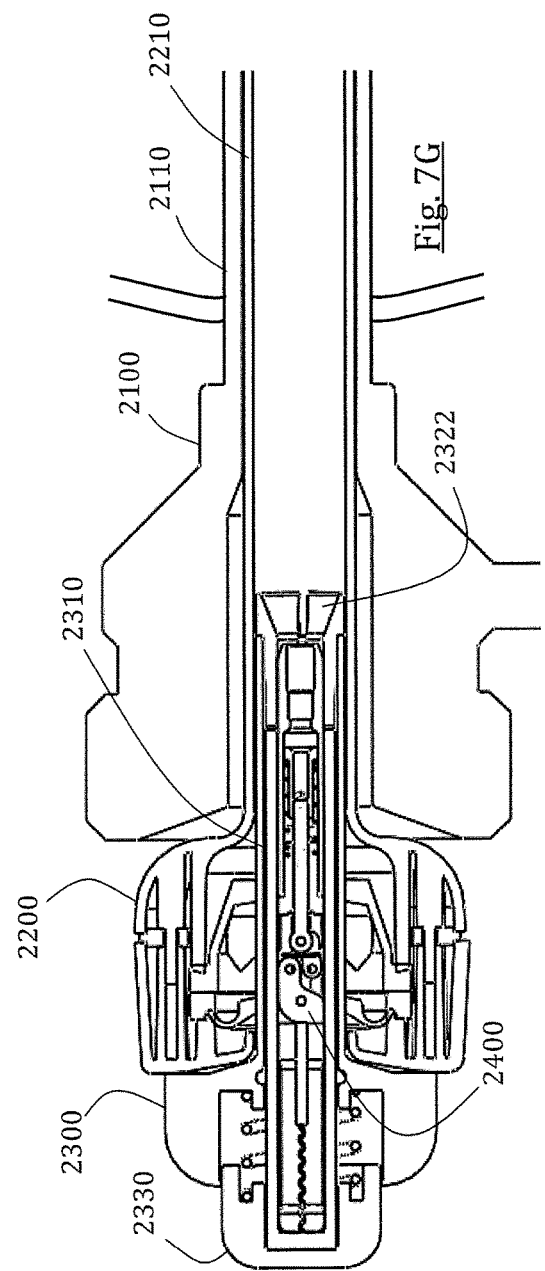

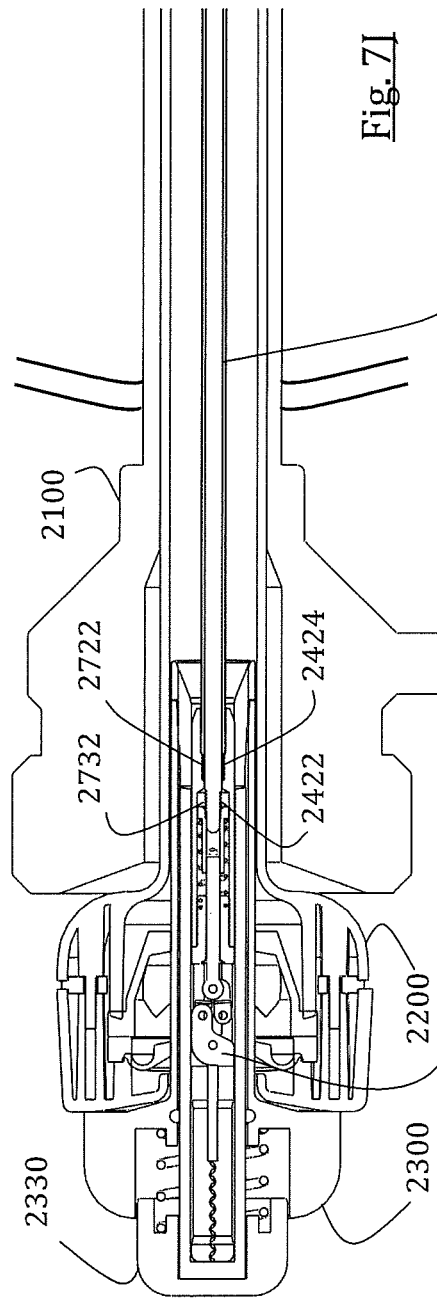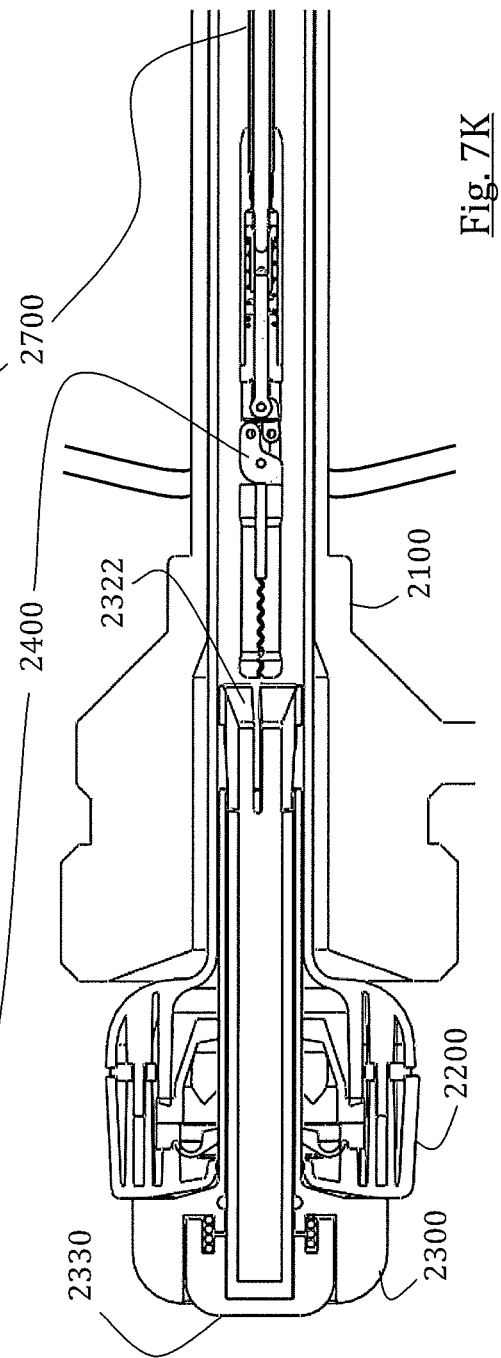

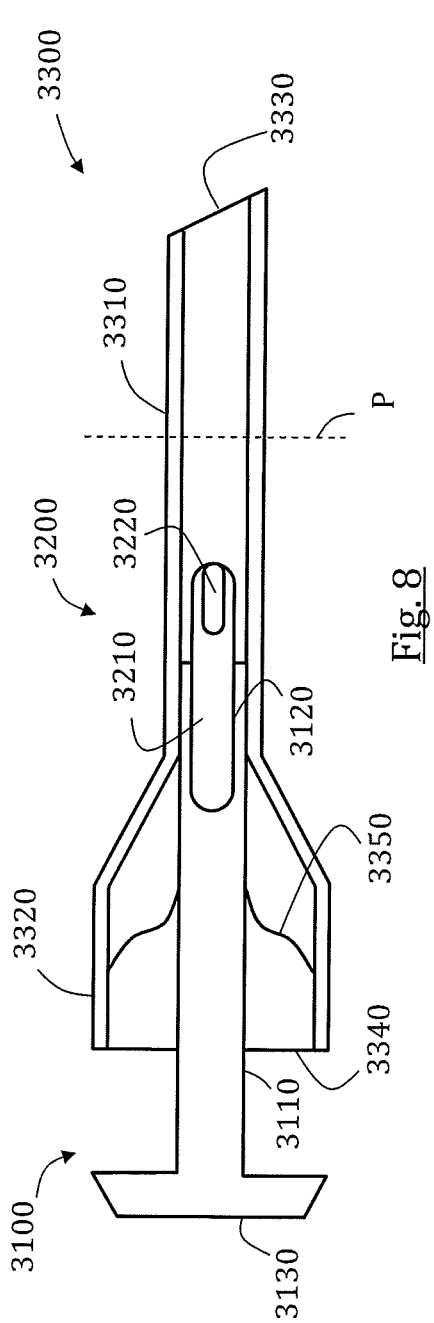
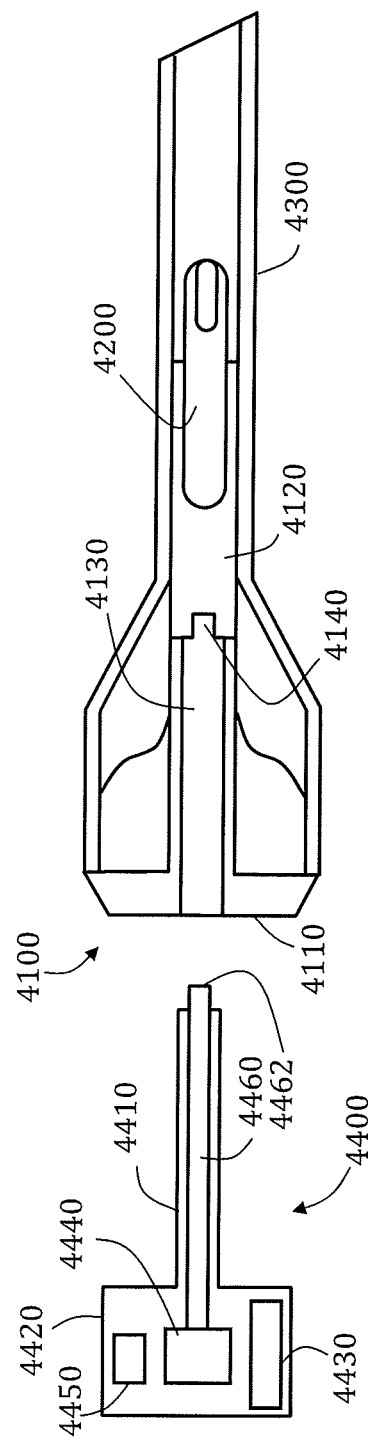
Fig. 8
Fig. 9

SURGICAL TOOL INTRODUCER

CROSS-REFERENCE TO RELATED APPLICATIONS

This application is a divisional patent application of U.S. patent application Ser. No. 14/188,095, filed on Apr. 24, 2014, which claims priority to U.S. Provisional Patent Application No. 61/768,846, filed Feb. 25, 2013, the disclosures of which are incorporated by reference in their entirety.

FIELD OF THE INVENTION

The present invention generally relates to systems and methods for surgeries preparations, and more specifically to methods and devices for assembling laparoscopic surgical instrumentation in a patient's body cavity.

BACKGROUND OF THE INVENTION

In laparoscopic surgery, several relatively small ports are made in the abdomen for allowing introduction of different types of instrumentation and accessories into the abdominal cavity for different surgical interventions (usually performed under endoscopic vision). Although usually considered superior in several aspects to open surgery, the use of a plurality of 5 to 15 mm ports still leads to local pain, scars, and possibly port related complications such as hernia in scars and the need for one or two assistants in addition to the surgeon. A known concept which aims at relieving some of such disadvantages includes the use of a single port for introducing regular sized surgical heads which are interchangeably connectable to manipulators extendable into the abdominal cavity via small sized entry points, usually 3 mm or less. The manipulators usually includes an elongated slender shaft being 3 mm or less in diameter, emerging from a robotic or handheld actuator part provided outside patient body, and they are introduced into the abdominal cavity either percutaneous (if having sharp distal end, for example) or through a minimal invasive laparoscopic port. Prior publications describing relevant techniques and instrumentation include: U.S. Pat. Nos. 5,352,219, 5,441,059, 5,593,402, 6,723,043, 7,666,181 and 8,133,254.

Nevertheless, assembling any two parts projecting from remote entry points in a body cavity still possesses certain challenges that should be answered in further improvement of currently proposed means and methods. One challenge is to safely engage and then assemble these two parts, even under laparoscopic vision, without possibly harming nearby tissues and organs and of course without dropping any of these parts before or during engagement and/or assembly in the body cavity. Second challenge is to locate, engage and assemble the two parts easily and rapidly so that no significant burden will be added to surgeon's work.

SUMMARY OF THE INVENTION

The present invention generally relates to systems and methods for surgeries preparations, and more specifically to methods and devices for assembling and/or disassembling laparoscopic surgical instrumentation in a patient's body cavity.

In an aspect of some embodiments, there is provided a tool introducer which comprises or is configured for introduction in an elongated body comprising a tubular body, for example a straight tube. In some embodiments, the tube encloses a tube lumen opened at its distal end with a tube opening. Optionally, the tube is sized and shaped for introducing in a body cavity via a laparoscopic port. In some embodiments, the tube is extendable through and from the laparoscopic port by at least 5 cm, optionally by at least 10 cm, optionally by at least 15 cm, optionally by at least 20 cm, or higher, or lower, or by any intermediate value.

Optionally, the elongated body includes an enlarged portion sized and/or shaped for barricading by the laparoscopic port. In some embodiments, a seal member is provided in or proximal to the lumen for sealing gas flow therefrom from a distal environment (such as the body cavity) to a proximal environment (such as an outer environment to the body cavity).

In some embodiments, the tool introducer includes locking means configured to selectively lock or unlock an interchangeable surgical tool to the tube from displacing axially and/or rotationally in the tube lumen. Optionally, the locking means are configured such that, at locking, a tool connector of the tool projects towards the tube opening and distanced therefrom by at least 3 cm, optionally by at least 5 cm, optionally by at least 10 cm, optionally by at least 20 cm, or higher, or lower, or any intermediate value. Optionally, the locking means are selectively introducible in the lumen, optionally as part of a plug member, and fixedly connectable to the tube. The locking means may include at least two opposing teeth selectively movable from an inward position when at locking to an outward position when at unlocking. Optionally, the locking means are normally locking. Optionally, the locking means are manually operational with a button provided at or adjacent the enlarged portion.

In some embodiments, the tool introducer includes visualization means or allows introduction of such via the lumen. Optionally and additionally, the tool introducer includes lighting means or allows introduction of such via the lumen.

In some embodiments, the tool is connectable with the tool connector to a fitting portion of a tool manipulator. Optionally, the fitting portion is located at a distal end of an elongated shaft. In some embodiments, the elongated shaft has a maximal diameter equal or smaller than 3 mm, optionally equal or smaller than 2 mm. In some embodiments, the tool manipulator and/or elongated shaft are introducible into the body cavity via an entry point remote to tool introducer entry. Optionally, the entry point is maintained by a second laparoscopic port or is made by percutaneous progression of the elongated shaft through a body cavity wall enclosing the body cavity.

In an aspect of some embodiments, there is provided a method, comprising at least one of the following steps (not necessarily in same order):

positioning a surgical tool introducer such that a distal portion thereof projects in a body cavity. Optionally, the tool introducer comprises or is being introduced into a straight tube, such as an engager or trocar, enclosing a tube lumen opened at its distal end with a tube opening. Optionally, the tool introducer includes locking means provided in the tube lumen to selectively lock or unlock an interchangeable surgical tool to the tube from displacing axially and/or rotationally. Optionally, the tool includes a tool connector projecting towards the tube opening and distanced therefrom by at least 3 cm. Optionally, the tool introducer positioning includes telescopic introduction through a laparoscopic port;

penetrating, either percutaneously, or through a trocar, with an elongated shaft of a tool manipulator in the body cavity via an entry point remote to the tool introducer. In some embodiments, the elongated shaft includes a fitting portion connectable with the tool connector of the tool. Optionally, the elongated shaft is sized and shaped to advance in the tube lumen at least until an adjoining of the fitting portion and the tool connector is applicable;

manipulating and/or extending the tool introducer to reach and engage the elongated shaft;

inserting the elongated shaft in the tube lumen via the tube opening;

advancing the elongated shaft in the tube lumen so that the elongated shaft and tool substantially aligns. Optionally, the fitting portion is also positioned in direct contact with the tool connector. In some embodiments, the advancing is preceded by positioning an interchangeable surgical tool in the tube lumen such that the tool connector projects towards the tube opening and distanced therefrom by at least 3 cm;

connecting the tool to the elongated shaft, optionally by adjoining the tool connector and the fitting portion; and withdrawing the elongated shaft from the tube lumen, optionally following unlocking the tool.

In some embodiments, the step of manipulating and/or the step of extending is preceded by at least one of introducing visualization means in the tube lumen and applying the visualization means to locate the elongated shaft in the body cavity. In some embodiments, the visualization means are removed before performing the positioning.

Optionally, at least one of the manipulating, extending and inserting is visually monitored.

In some embodiments, the method also includes removing of the tool. Optionally the tool removal includes at least one of the following steps:

re-inserting the elongated shaft in the tube lumen via the tube opening;

re-advancing the elongated shaft with the tool in the tube lumen so that the elongated shaft and tool substantially aligns and optionally becomes in contact with the locking means;

disconnecting the tool from the elongated shaft by dispatching the tool connector and the fitting portion. Optionally, disconnecting is preceded by shifting the locking means to unlocking mode. Optionally, the unlocking is followed by returning the locking means to locked mode and locking the tool to the tube; and withdrawing the elongated shaft from the tube lumen.

In an aspect of some embodiments, there is provided a system which includes an elongated tube, comprising a tube proximal opening, a tube distal opening, a tube lumen extending between the tube proximal opening and the tube distal opening. In some embodiments, the elongated tube has a proximal segment and distal segment, and optionally the proximal segment has a larger outer diameter than the distal segment. Optionally, a seal provided in the the lumen, optionally a zero seal and/or an instruments seal. In some embodiments, the system also includes a tool holder which includes locking means to selectively lock or unlock an interchangeable surgical tool from displacing axially and/or rotationally in the tube lumen. In some embodiments, the elongated tube is telescopically introducible at a port proximal end, through a port lumen and bypassing a seal mechanism of a laparoscopic port interconnecting a body cavity and an outer environment. In some embodiments, the tool holder is adapted to be inserted through the tube proximal opening to be deployed in the tube lumen and thereby projecting a tool connector of the tool towards the tube distal opening and in a distance of at least 3 cm therefrom.

In some embodiments, the tool holder comprises a holder distal opening, a sealed proximal end and a holder lumen extending at least partially therebetween.

In some embodiments, the holder lumen is adapted to receive an end portion of a needle system when the needle entering the tube distal opening via the port distal opening.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 schematically illustrates a cut view representing an exemplary system for introducing a surgical tool in a body cavity via a laparoscopic port and for engaging with, aligning and assemble the surgical tool to a tool manipulator in the body cavity, in accordance with an exemplary embodiment of the present invention;

FIG. 6 schematically illustrates a cut view representing an exemplary tool holder member of the exemplary system represented in FIG. 5, in accordance with an exemplary embodiment of the present invention;

FIGS. 7A-K schematically illustrate cut views representing different stages of deploying a laparoscopic surgical tool using the exemplary system represented in FIG. 5, in accordance with an exemplary embodiment of the present invention;

FIG. 8 schematically illustrates a cut view representing a tool introducer introducible in a laparoscopic port, in accordance with an exemplary embodiment of the present invention; and FIG. 9 schematically illustrates a cut view representing a tool introducer with powered tool deployer, in accordance with an exemplary embodiment of the present invention.

DETAILED DESCRIPTION

The present invention generally relates to systems and methods for surgeries preparations, and more specifically to methods and devices for assembling laparoscopic surgical instrumentation in a patient's body cavity.

In an aspect of some embodiments, there is provided a device or a "tool introducer" for introducing surgical tools into a patient's body cavity, such as an abdominal cavity. Surgical tools according to present disclosure may include any surgical tool known to art having outer diameter generally being equal or smaller than 20 mm, or equal or smaller than 10 mm, or in some exemplary embodiments being substantially between 3 mm to 5 mm in outer diameter. As such, surgical tools according to present disclosure may include but not be limited to graspers, coagulators, hooks, staplers, scalpels, suturing means, heat or light sources, surgical monitoring devices, scissors, needle holders, retractors, clip applicators or others. In some embodiments, surgical tools according to present disclosure are surgical heads connectable to manipulators, which may be either manually or robotically operable. In some embodiments, surgical heads according to present disclosure are interchangeable in the sense that different surgical heads can be connected, sequentially, onto a single manipulator. Manipulators according to present disclosure generally include an elongated shaft, optionally needle like, with means to connect to and actuate the surgical head. Connection between surgical head and elongated shaft may include any type of connection means such as but not limited to snap locking, elastic teeth, threading, bayonet locking, clamp/chuck connection, ball and socket, magnet, friction, expandable portion (e.g., balloon member), or others. In some embodiments, such elongated shafts are generally 5 mm or less in diameter, optionally 3 mm or less, optionally 2 mm or less, or higher, or lower, or in any intermediate value.

In some embodiments, the tool introducer includes or is introducible in an elongated sleeve or tubular member (optionally, though not necessarily, cylindrical) in which the elongated shaft may be inserted for assembling or disassembling with the surgical heads positionable and lockable therein. In some embodiments, surgical tool docking and/or locking position in the tool introducer is distant enough from its distal opening therefore forcing the elongated shaft of the manipulator to align at least partially so that easier assembling condition is met. In some such embodiments, distance from distal opening may be at least 3 cm, optionally at least 5 cm, optionally at least 10 cm, optionally at least 20 cm. In some embodiments, assembling or disassembling is possible in the body cavity, optionally and alternatively outside patients body, or optionally anywhere in between.

Figure 1:
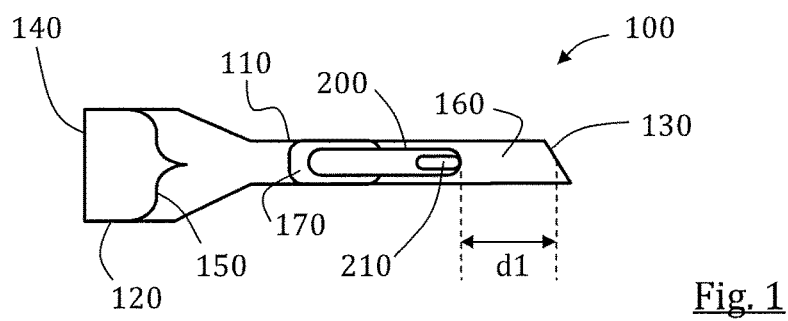
FIG. 1 schematically illustrates a cut view representing a tool introducer, in accordance with an exemplary embodiment of the present invention.

Reference is made to FIG. 1 which schematically illustrates a cut view representing a tool introducer 100, in accordance with an exemplary embodiment of the present invention. Tool introducer 100 includes an elongated body comprising a straight tube 110, the tube enclosing a tube lumen 160 opened at its distal end with a tube opening 130. Tool introducer 100 also includes locking means 170 which are provided in tube lumen 160 to selectively lock or unlock an interchangeable surgical tool 200 to tube 110 from displacing axially and/or rotationally.

In some embodiments, the locking means are configured such that, at locking, a tool connector 210 of the tool 200 projects towards tube opening 130 and distanced with a distance d1 therefrom being at least 3 cm, or optionally by at least 5 cm, or optionally by at least 10 cm, or optionally by at least 20 cm, or higher, or lower, or any intermediate value.

Tool introducer 100 includes a seal member 150 provided in or proximal to lumen 160 for sealing gas flow therefrom from a distal environment to a proximal environment, so, for example, inflation gas (normally $CO_2$) will not escape abdominal cavity during tool introduction and/or assembly/disassembly. Seal member 150 may be permanent or selectively removable, may be firm or pliable (e.g., a valve) or have any form as known in the art. Tool 200 may be readily provided in lumen 160 or can be introducible thereto via tube's proximal opening 140, optionally with or without locking means 170.

Tool introducer 100 may be deliverable into the body cavity via a premade cut or puncture, or it may be introduced in a percutaneous fashion while penetrating and piercing through tissues from the outer environment and into the inner environment enclosed in the body cavity. Optionally and alternatively, tool introducer 100 is introducible via a laparoscopic port so, optionally, tube 110 is sized and shaped for introducing in a body cavity via a laparoscopic port. In some embodiments, and as shown in FIG. 1, tool introducer 100 includes an enlarged portion 120 sized and/or shaped for barricading by a laparoscopic port.

Figure 2A:
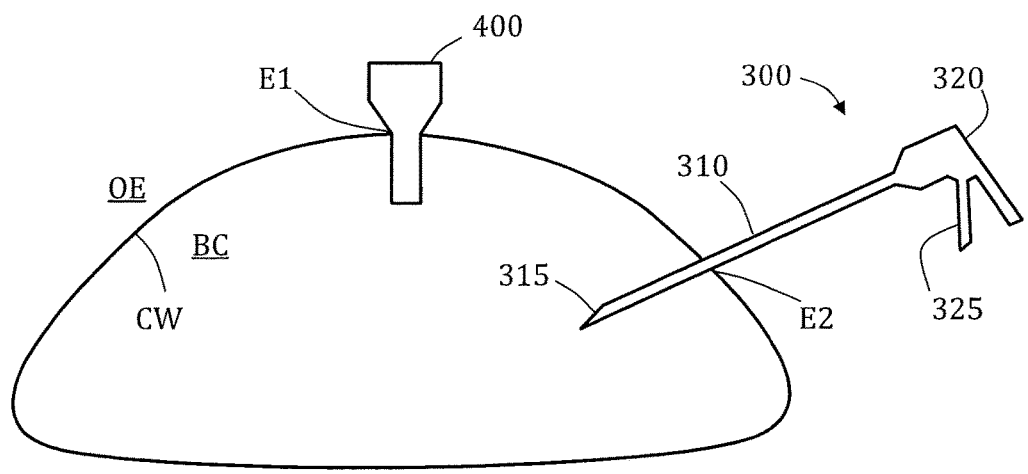
FIGS. 2A-D schematically illustrate cut views representing different stages of deploying a laparoscopic surgical tool, in accordance with an exemplary embodiment of the present invention.
Figure 2B:
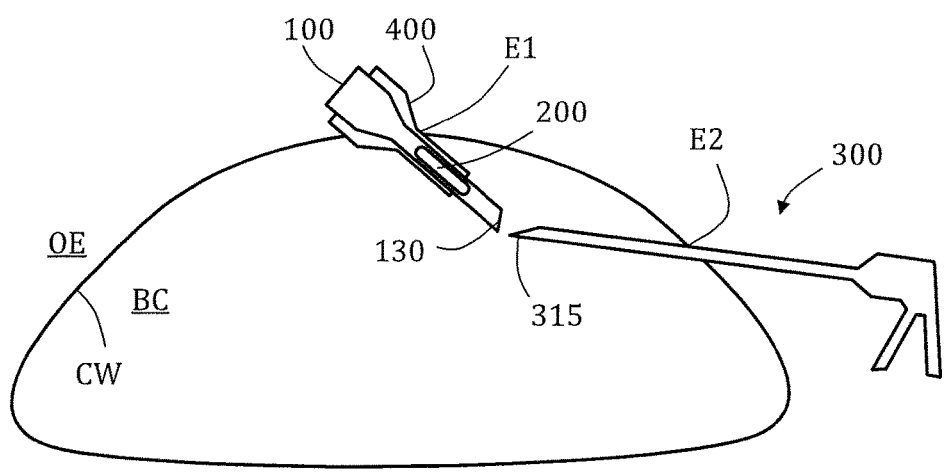

Reference is now made to FIGS. 2A-D which schematically illustrate cut views representing different stages of deploying surgical tool 200, in accordance with an exemplary embodiment of the present invention. In the suggested method, tool 200 is introduced from outer environment OE into body cavity BC through body cavity wall CW so that it can be connected while in body cavity BC to a distal end portion 315 of a manipulator 300. As shown in FIG. 2A, a laparoscopic port 400 is provided in body cavity wall CW, through a first entry point E1, thereby creating a selectively sealed passage between body cavity BC and an outer environment OE. Laparoscopic port 400 may be of any type known to art, a trocar, a sheath or other, with means to connect to a gas pressurizing source and to seal gas backflow therethrough. In some embodiments, laparoscopic port 400 allows passing therethrough of objects (such as tools and instruments) that if aligned with its elongated axis has external boundaries of about 20 mm or less in diameter, or optionally about 10 mm or less in diameter or optionally about 5 mm or less in diameter. In some embodiments, laparoscopic port 400 is the largest laparoscopic port provided in cavity wall CW during surgery to introduce large or normal size surgical tools in body cavity BC. Optionally and alternatively, laparoscopic port 400 is the single laparoscopic port used during surgery hence other means (e.g., manipulators) may be introduced in body cavity BC otherwise, such as by percutaneous penetration through cavity wall CW. In some embodiments, if body cavity BC is an abdominal cavity, first entry point E1 may be the umbilicus. Laparoscopic port 400 introduction and setting may be done as commonly practiced in laparoscopic surgery.

Before, after or in parallel to providing laparoscopic port 400 in first entry point E1, tool manipulator 300 is introduced as well and deployed in body cavity BC. Tool manipulator 300 includes an elongated shaft 310 ending distally with end portion 315 and with a proximal handheld part 320 having at least one actuating member 325. Elongated shaft 310 penetrates into body cavity BC through a second entry point E2, being substantially remote to first entry point E1. In some embodiments, end portion 315 is sharp such that it can be used to pierce through a percutaneous passage through body cavity wall CW at second entry point E2. Elongated shaft 310 comprises a fitting portion (not shown) connectable with a tool connector of a surgical tool (such as tool connector 210 of tool 200). Elongated shaft 310 is sized and shaped such so it can be advanced in a tube lumen (such as lumen 160 of tool introducer 100), at least until an adjoining fitting portion and tool connector is applicable.

As shown in FIG. 2A, tool introducer 100 equipped with tool 200 is passed via laparoscopic port 400 such that tube 110 projects in body cavity BC and tube opening 130 is opened to body cavity BC. Before, during or after such passing of tool introducer 100 through laparoscopic port 400, visualization means (not shown) can be used in order to trace elongated shaft 310 and/or its distal end 315. Such visualization means may include any of a laparoscope, endoscope, optical fiber, and a camera, optionally accompanied with illumination means, and these may be provided as an integral part of tool introducer 100 or laparoscopic port 400, or can be inserted as a separate device via tool introducer 100 or laparoscopic port 400. Tool introducer 100 is then manipulated and/or extended, under vision or blindly, in order to reach and engage elongated shaft 310 and/or its distal end 315. In some embodiments, tube 110 is extendable through and from laparoscopic port 400 by at least 5 cm, optionally by at least 10 cm, optionally by at least 15 cm, optionally by at least 20 cm. Optionally and alternatively (not shown), the visualization means are introduced from a separate entry point into body cavity BC and can be used to survey engagement and connection of the system components as described below, from the side.

Figure 2C:
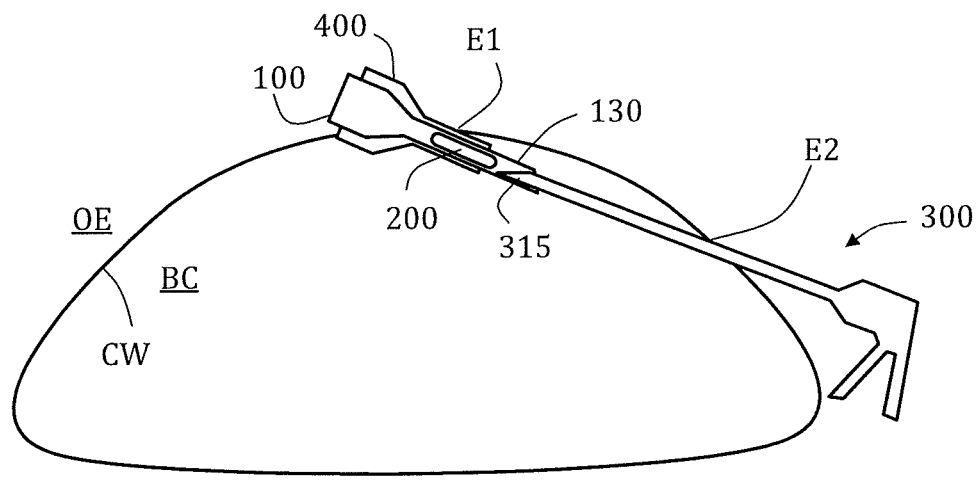
Figure 2D:
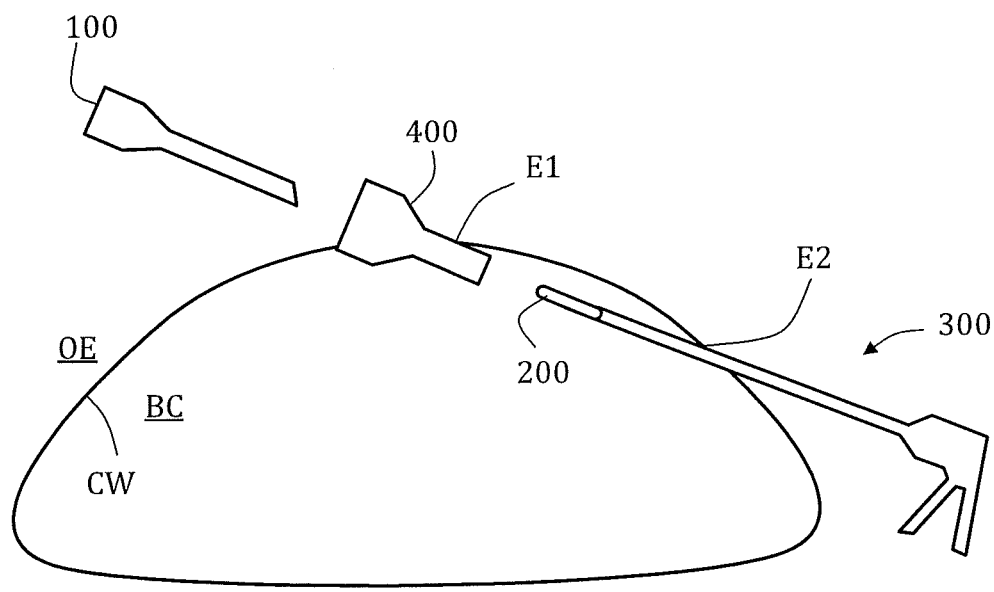

As shown in FIG. 2C, elongated shaft 310 is inserted in tube lumen 160 via tube opening 130 and then advanced therein so that elongated shaft 310 and tool 200 substantially aligns, optionally forced to align by bounded geometries of elongated shaft 310 in tube 110. Elongated shaft is advanced until assembly with tool 200 is possible, optionally when the fitting portion of elongated shaft 310 is in direct contact with tool connector 210. Tool 200 may then be connected to elongated shaft 310 by adjoining tool connector and fitting portion. As shown in FIG. 2D, manipulator 300 may then be withdrawn so that elongated shaft 310 is removed from tube lumen 160, and the assembled surgical instrument can be applied for surgery as needed. Optionally, tool 200 is first unlocked from tool introducer 100 before manipulator 300 can be withdrawn. Tool introducer 100 may be kept in laparoscopic port 400 or removed therefrom (as shown), optionally replaced with a second tool introducer equipped with another tool for connecting to a second manipulator (not shown).

Figure 3A:
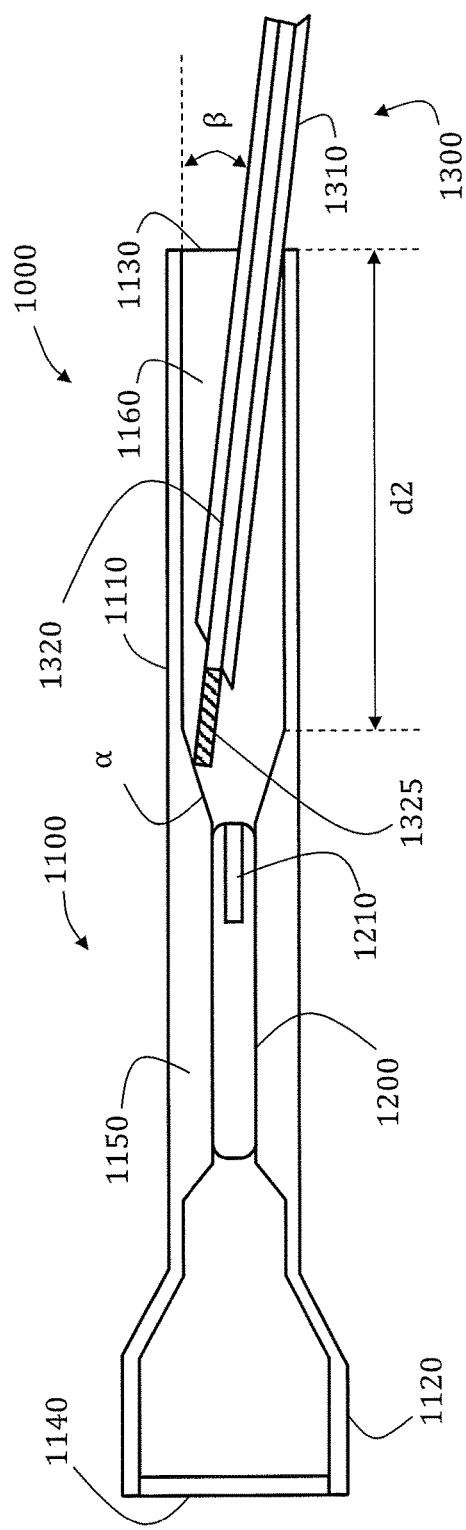
FIGS. 3A-B schematically illustrate cut views representing use of an exemplary tool introducer for aligning between a surgical head and a manipulator distal end in a safe environment, in accordance with an exemplary embodiment of the present invention.
Figure 3B:
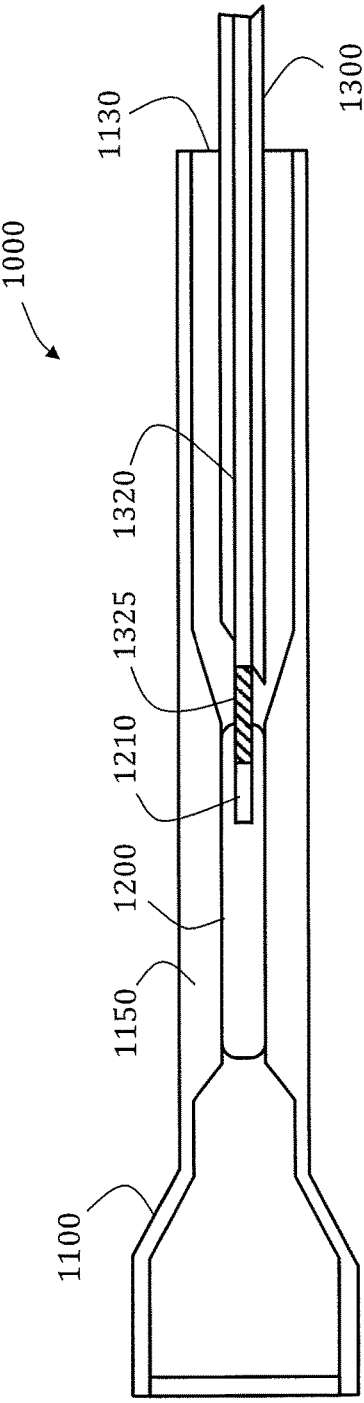

Reference is made to FIGS. 3A-B which schematically illustrate cut views representing use of an exemplary tool introducer 1100 in a laparoscopic system 1000 for aligning between a surgical head 1200 and a manipulator distal end 1300 in a safe environment, in accordance with an exemplary embodiment of the present invention. Tool introducer 1100 includes an elongated tubular body 1110 having an enlarged portion 1120 ending with a sealed proximal end 1140, and a distal end 1130 opened to inner lumen 1160. In lumen 1160 with distance d2 from distal opening 1130 there is a docking portion 1150 which selectively locks to surgical head 1200 shown nests therein. Docking portion 1150 opens distally with an angle α for allowing centering of incoming slender artifacts sliding therein until reaching and arriving in direct contact with connector 1210 of surgical head 1200. Manipulator 1300 includes an inner member 1320 and an outer member 1310 which may be fixed or rotatable and/or slidable on with the other. At least inner member 1320 includes a fitting portion at its distal tip, namely thread 1325 that can be threaded in connector 1210 having mating thread for bolt-and-nut type connection. Distance d2 is chosen such to achieve a maximally allowed angle of attack β when thread 1325 is adjacent docking portion 1150 entry, in order to assist in accurate positioning therein. In some embodiments, angle β is equal or smaller than about 45°, optionally equal or smaller than about 30°, optionally equal or smaller than about 15°, optionally equal or smaller than about 5°, or higher, or lower, or of any intermediate value. In some such embodiments, angle β depends on distance d2 as well as in geometrical ratios between lumen 1160 size and manipulator outer boundaries dimensions. In some embodiments, distance d2 is at least 3 cm, optionally at least 5 cm, optionally at least 10 cm. In some embodiments, lumen 1160 diameter distal to docking portion 1150 is between 10 mm and 1 mm, optionally between 7 mm and 2 mm, optionally between 5 mm and 3 mm. In some embodiments, outer diameter of manipulator distal end 1300 is equal to or smaller than about 3 mm, optionally equal to or smaller than 2 mm, optionally about 1.5 mm.

As shown in FIG. 3A, manipulator distal end 1300 advances in lumen 1160 and reaches docking portion 1150. Lumen boundaries imposed by tubular body 1110 are rigid yet smooth enough so that manipulator 1300 would not stuck or cling in-place, while providing a tracked passage thereinside while preventing possible harm to organs or tissues outside tubular body 1110 which may potentially happen in case the surgeon would target manipulator distal end 1300 directly to a small opening such as of surgical head connector 1210. After manipulator distal end 1300 is advanced in lumen 1160 and forced to align thereto, connection with surgical head 1200 can then be made, as shown in FIG. 3B. In some embodiments, entire manipulator end portion 1300 or only inner member 1320 revolves so that thread 1325 threads into connector 1210.

Figure 4A:
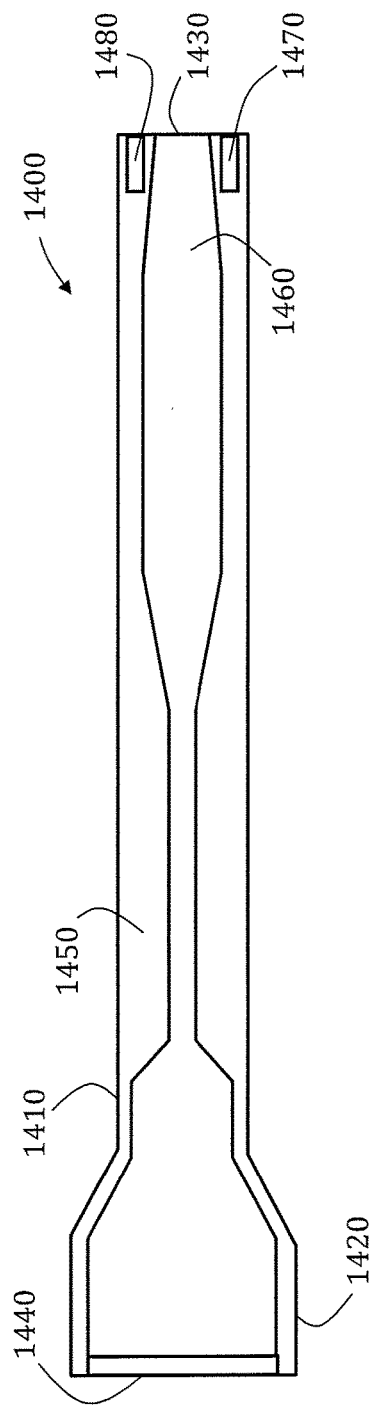
FIGS. 4A-B schematically illustrate cut views representing two exemplary tool introducers with different visualization means, in accordance with an exemplary embodiment of the present invention.
Figure 4B:
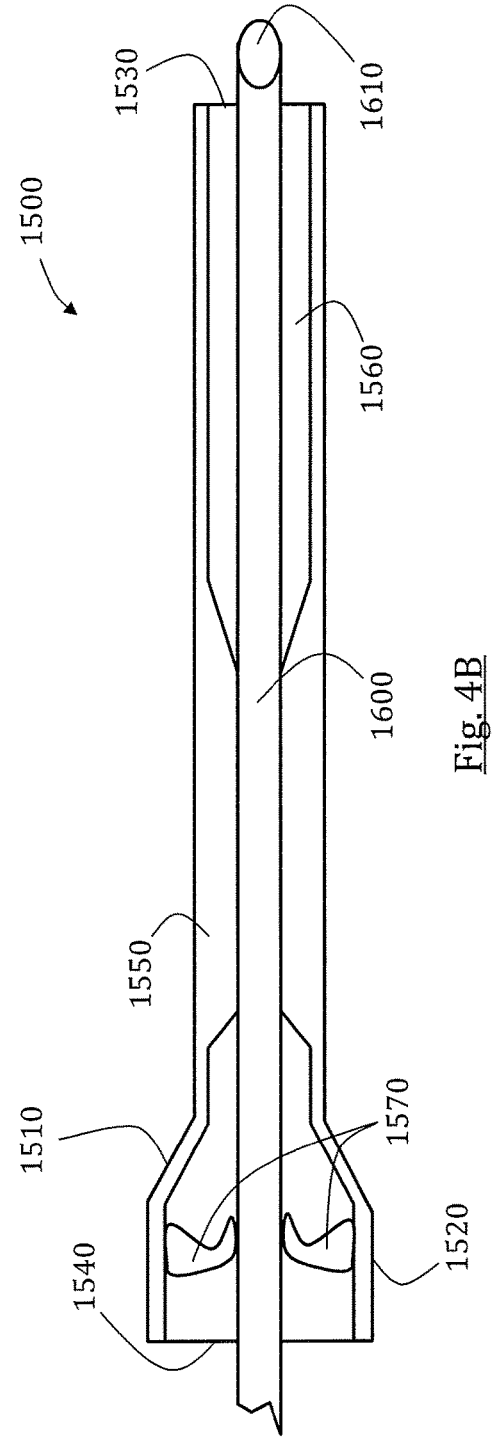

FIGS. 4A-B schematically illustrate cut views representing two exemplary tool introducers 1400 and 1500 with different visualization means, in accordance with an exemplary embodiment of the present invention. As shown in FIG. 4A, tool introducer 1400 includes an elongated tubular body 1410 having an enlarged portion 1420 ending with a sealed proximal end 1440, and a distal end 1430 opened to inner lumen 1460. A docking portion 1450 is provided in lumen 1460 which can selectively lock to a surgical head (not shown). Tubular body 1410 at its distal end around opening 1460 encloses at least one visual capture device 1470 (e.g., digital camera head) and at least one illumination source 1480 (e.g., LED illumination) which may be operational wired or wirelessly to power source and/or image recording unit provided outside patient's body. As shown in FIG. 4B, tool introducer 1500 includes an elongated tubular body 1510 having an enlarged portion 1520 ending with a selectively sealed proximal end 1540, housing a valve 1570, and a distal end 1530 opened to inner lumen 1560. A docking portion 1550 is provided in lumen 1560 which can selectively lock to a surgical head (not shown). An optical fiber 1600 is shown when introduced through lumen 1560 that is configured to transfer image and light from its tip 1610 backwards to image capture and recording means (not shown) provided outside patient's body.

In some embodiments, a tool introducer is provided as a system or a kit which comprises an elongated tubular member (tube) or sleeve for reaching and engaging a distal end of a tool manipulator, and a separate drawer and/or tool locking means that can be inserted from a proximal opening of the tube and deliver a tool therein to a predefined position having a minimal distance from tube's proximal opening, as previously described. As such, systems or kits according to the present disclosure may include locking means that are selectively introducible in tube's lumen, optionally as part of a plug member, and fixedly connectable to the tube. In some such embodiments, locking means may include at least two opposing teeth selectively movable from an inward position at locking to an outward position at unlocking. Optionally, the locking means are normally locking. Optionally, the locking means are manually operational with a button mechanism. Optionally, the tube is sized and configured for passing through a laparoscopic port, such as a commercially available laparoscopic port having inner diameter between 3 mm and 20 mm, or optionally between 5 mm and 10 mm.

Reference is now made to FIG. 5 which schematically illustrates a cut view representing an exemplary system 2000 for introducing a surgical tool in a body cavity via a laparoscopic port 2100 and for engaging with, aligning and assemble the surgical tool to a tool manipulator (not shown) in the body cavity, in accordance with an exemplary embodiment of the present invention. System 2000 includes an engager 2200 and a tool holder 2300. In FIG. 5, tool holder 2300 is shown equipped with an interchangeable grasper 2400 and provided in and assembled to engager 2200; and both are provided in and through laparoscopic port 2100.

System 2000 may be sold or provided to the surgical team as a kit comprising at least one engager 2200 (shown in detail in FIG. 7B) and at least one tool holder 2300 (shown in detail in FIG. 6). The kit may also include laparoscopic port 2100 (shown in detail in FIG. 7A) or be configured to work with commercially available ports. The kit may also include at least one surgical tool, optionally including but not limited to interchangeable grasper 2400 (shown in detail in FIG. 7D). The kit may also include at least one tool loader, optionally including but not limited to a grasper loader 2600 (shown in detail in FIGS. 7D-E). The kit may also include at least one manipulator comprising a needle portion, optionally including but not limited to needle 2700 (shown in detail in FIG. 7I).

Laparoscopic port 2100 includes an elongated tubular member or tube 2110 enclosing a lumen 2120 and having a proximal enlarged handheld portion 2130. Handheld portion allows introduction of objects therethrough into body cavities when deployed via proximal port opening 2140 and includes at least one seal such as port seal 2150 to prevent gas escape. Pressure inlet 2160 allows connection to a pressurized gas source. Laparoscopic surgery involves insufflation of a gas (usually carbon dioxide) into the abdominal/peritoneal cavity producing a pneumoperitoneum. This causes an increase in intra-abdominal pressure (IAP). Carbon dioxide is commonly insufflated into the peritoneal cavity for example at a rate of 4-6 liter/min to a pressure of 10-20 mm Hg, for example. The pneumoperitoneum may be maintained for example by a constant gas flow of 200-400 ml/min.

Engager 2200 includes an elongated tubular body 2210 opened at a proximal end 2240 and at a distal end 2270 with a lumen 2220 extending therebetween. According to the present disclosure, elongated tube 2200 includes at least one seal provided in lumen 2220 such as a zero seal 2260 (configured to prevent gas passage at least when it is absent from any object extending therethrough) and an instruments seal 2250 (configured to prevent gas at least when objects having outer diameter of a certain diameter range extends therethrough). Optionally and as shown, at its distal end 2270 there is provided an expandable funnel, optionally and as shown, an asymmetrical funnel component 2212. In some embodiments, funnel 2212 is a self-expandable partially (or, alternatively, fully) conic structure, expandable from and re-collapsible to a substantially tubular form. At its tubular form, funnel 2212 can be passed at both directions through laparoscopic port lumen 2120. At its expanded conic form, funnel 2212 has a substantially greater span which increases covering area around any intruding slender objects, such as a distal end portion of a manipulator longitudinal shaft. Furthermore, the expanded funnel 2212 facilitates a more smoother introduction and accommodation of a nonaligned shaft (e.g., projecting at an angle between 100-180° of any coordinate axis with respect to engager tube's longitudinal axis) so that instead of impinging and even penetrating through the funnel, the needle can gently slide over the curved walls of the funnel until aligning with its longitudinal axis. With its configuration, including a tapered edge and having a first closed side and a second substantially opened side, funnel 2212 allows a continuous accurate visualization and monitoring using an endoscope or a camera projected forward. Such a design further allows a faster and easier recollapsing of funnel 2212. As shown in FIG. 5 and in FIG. 7B, tube body 2210 is telescopically introducible at proximal end 2140 of laparoscopic port 2100, through lumen 2120 and bypassing seal 2150, yet maintaining sealed passage to gas passage therein (with seals 2250 and/or 2260) or between its outer boundaries and seal 2150.

Tool holder 2300 includes an inner sleeve member 2320 slidable in an outer sleeve member 2310. Outer sleeve member 2310 has an enlarged proximal end portion 2312 with a concavity fitted for a push-button 2330. Button 2330 is connected to proximal end of inner sleeve member 2320 and is interconnected with compression spring 2332 to outer sleeve member 2310 so that is normally pulled back with respect to outer sleeve member 2310 when not pushed in. Tool holder 2300 includes locking means 2326 to selectively lock or unlock an interchangeable surgical tool from displacing axially and/or rotationally in engager tube lumen 2220. In some embodiments and as shown, locking means 2326 include a distal portion of inner sleeve member 2320 that is slitted partially along its length with slits 2324 so that to create a plurality of teeth 2322 configured to extend outwardly from longitudinal axis when emerging out of outer sleeve member 2310 (when button 2330 is pushed). When button 2330 is at backward position (pulled back) teeth 2322 are inwardly compressed and nest within the boundaries imposed by outer sleeve member 2310, so that in case an surgical tool is housed in tool holder 2300 (as shown for example in FIG. 7G) the inwardly compressed teeth locks the tool in-place. In some embodiments, and as shown in FIG. 5 and in FIG. 7G, tool holder 2300 is adapted to be inserted through engager's proximal opening 2240 to be deployed in lumen 2220 and thereby projecting a tool connector (such as connection threads 2422 and 2424 of interchangeable grasper 2400) towards engager's distal opening 2270. In some embodiments, a surgical tool, such as interchangeable grasper 2400, when placed with tool holder 2300 in and assembled with engager 2200, has its distalmost face distanced by at least 3 cm from distal end 2270 of engager 2200.

Interchangeable grasper 2400 includes a grasper portion 2410 and a connector portion 2420. Grasper portion 2410 includes a first jaw 2412 and a second jaw 2414 pivotally connected with a joint 2416. Connector portion 2420 includes an inner member comprising a first female thread 2422 slidable in an outer member comprising a second female thread 2424, larger in diameter than first female thread 2422. Relative distance between threads 2422 and 2424 determine relative distance between jaws 2412 and 2414 or magnitude of compression force developed therebetween. A compression spring 2426 keeps threads 2422 and 2424 in a nominal distance such that jaws 2412 and 2414 are kept closed (in-contact) yet with negligible compression.

Needle 2700 of manipulator (which is not shown in full) includes an inner rod member 2730 slidable in cylindrical member 2720. Inner rod member 2730 has a distal dull tip 2734 and a first male thread 2732 adjacent thereto. Cylindrical member 2720 includes a second male thread 2722 provided at its distal end. In some embodiments, needle 2700 is operable to create a percutaneous penetration path hence includes sharp means to puncture and cut through soft tissues. In some such embodiments, and as shown, needle 2700 includes an outer cover 2710 with sharp distal end in which cylindrical member 2720 may slide backwards along with inner rod member 2730 until fully retracted therein, so that needle 2700 acts similarly to a veress needle as needed.

Figure 7H:
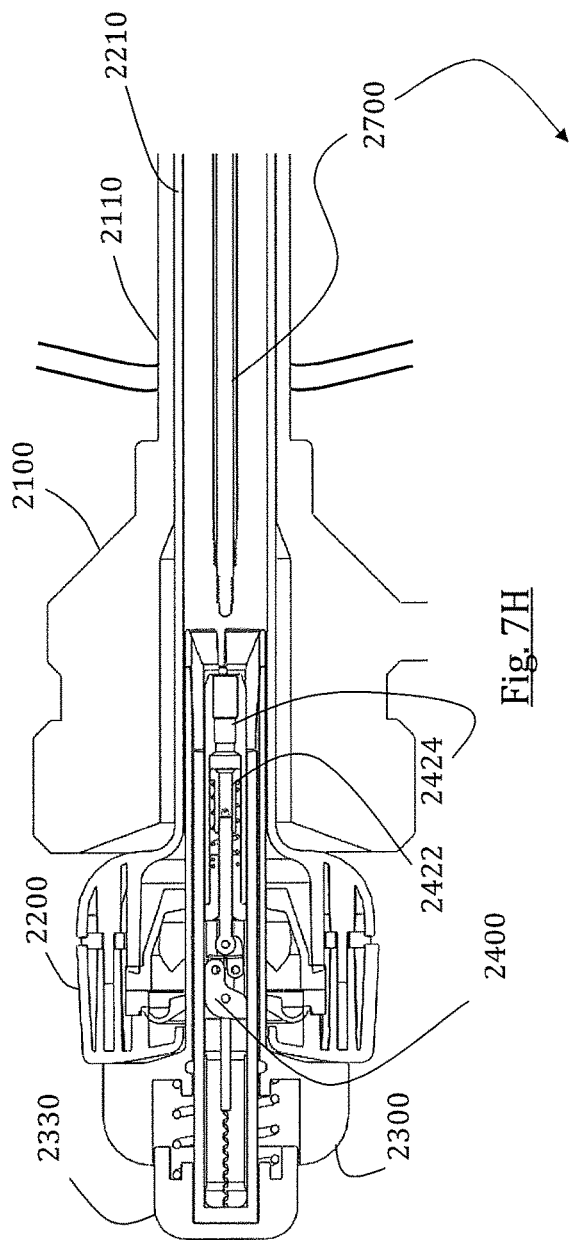
Figure 7I:
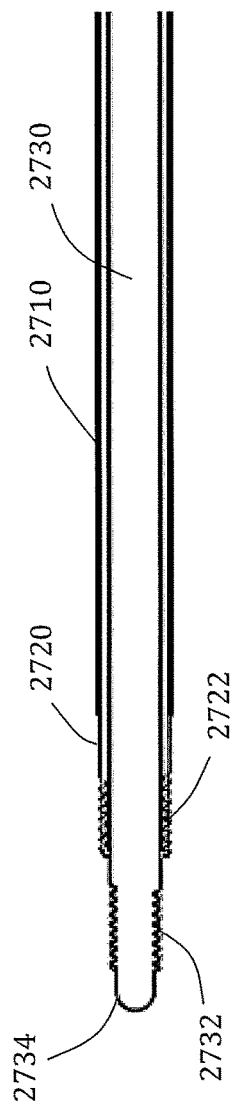

Reference is now made to FIGS. 7A-K which schematically illustrate cut views representing different stages of deploying interchangeable grasper 2400 using system 2000, in accordance with an exemplary embodiment of the present invention. As shown in FIG. 7A, laparoscopic port 2100 is introduced into body cavity BC through body cavity wall CW using known surgical practiced techniques. Body cavity BC may then be insufflated via pressure inlet 2160. As shown in FIG. 7B, engager 2200 is then passed in laparoscopic port 2100 bypassing its seal 2150 yet keeping a sealed environment using zero seal 2260. As shown in FIG. 7C, a laparoscope 2500 is introduced into body cavity BC via engager 2200 with its distal end 2510 peeping partially beneath and in funnel 2212, or upward or backward thereto. Laparoscope 2500 can be used to trace end portion of a manipulator (such as needle 2700 shown in FIGS. 7H-K) and visualize approaching and reaching it with funnel 2212. Once manipulator emerges into engager's lumen 2220, optionally while laparoscope 2500 is partially withdrawn, the laparoscope can be removed and further steps can optionally be made blindly.

Before, after or in parallel to the above-mentioned steps, interchangeable grasper 2400 may optionally be loaded in tool holder 2300 (in case it is not preloaded) using loader 2600. As shown in FIG. 7D, loader 2600 is bolted (optionally manually, using its enlarged end portion 2610) with a threaded portion 2620 into second female thread 2424 of interchangeable grasper 2400. Alternatively and optionally, loader may be plugged in into a recess such as second female thread 2424 of interchangeable grasper 2400 without threading. With loader 2600, interchangeable grasper 2400 is then pushed into tool introducer 2300 while its button 2330 is pushed so that teeth 2322 extend out from outer sleeve member 2310 and outwardly, so that to allow such loading (as shown in FIG. 7E) until interchangeable grasper 2400 is fully nesting in-position (as shown in FIG. 7F). Button 2330 may then be released to pop out, and loader unbolted and removed.

Afterwards, the loaded tool introducer 2300 is inserted (e.g., plugged-in or bolted) in engager 2200 via its proximal opening 2240, optionally instead of laparoscope 2500. Needle 2700 may then advance forward in engager lumen 2210 until reaching distal portion of interchangeable grasper 2400 (FIG. 7H). Connection is made possible, for example, if both inner rod member 2730 and cylindrical member 2720 revolves (e.g., clockwise) until first male thread 2732 is bolted in first female thread 2422 and second male thread 2734 is bolted in second female thread 2424 (FIG. 7J). Only then, button 2330 can be pushed and needle 2700, now equipped with interchangeable grasper 2400) can be withdrawn from tool holder 2300 and engager 2200 and be used in surgery as needed.

In some embodiments, different or similar tools can be loaded in same or different tool holder, using same or different loader, so same or different needles/manipulators. Tool holder 2300 can be removed and replaced with laparoscope 2500 for visualizing the surgical procedure.

Disassembly of interchangeable grasper 2400 from needle 2700 (or of other likewise instrumentation) can be done similarly in reverse fashion, for example by first using engager 2200 equipped with laparoscope 2500 to locate, reach and engage interchangeable grasper 2400. Then inserting the interchangeable grasper partially in engager 2200 and removing laparoscope 2500. Then inserting unloaded tool holder 2300 in engager 2200 and pushing interchangeable grasper thereto until contacting teeth 2322. In some embodiments, verification of correct contact is made (optionally, visually and/or tactilely and/or electronically or otherwise). In some embodiments, the pushing ends with preliminary locking such as by snap-locking means. Then, button 2330 is pushed and interchangeable grasper 2400 can be pushed further to nest in tool introducer 2300 and allow proper release of button 2330. Afterwards, the needle 2700 can be unbolted from interchangeable grasper 2400 and all instruments may be removed from patient's body or replaced as needed.

Reference is made to FIG. 8 which schematically illustrates a cut view representing a tool introducer 3100 introducible in a laparoscopic port 3300, in accordance with an exemplary embodiment of the present invention. Laparoscopic port 3300 may be a commercially available device provided with or separate to tool introducer 3100, from same or different vendor. Laparoscopic port 3300 may be a sheath or cannula of a laparoscopic trocar system having standard or non-standard sizes, for example an inner diameter of 5 mm, 8 mm, 11 mm, 12 mm or 15 mm, or higher, or lower, or intermediate size, and/or a length of 50 mm, 75 mm, 100 mm, 150 mm, 200 mm, or higher, or lower, or intermediate size. Laparoscopic port 3300 includes a hollow tubular body 3310 with a proximal wide portion 3320, a proximal end 3340 and a distal end 3330. A sealing mechanism 3350, commonly comprising zero seal and/or instruments seal, is configured for sealing inner passage of tubular body 3310 if empty or if occupied with artifacts, such as tool introducer 3100, passing therethrough.

Tool introducer 3100 includes an elongated body 3110 and locking means 3120 to selectively lock or unlock with an interchangeable surgical tool 3200 from moving or displacing axially and/or rotationally. Tool introducer 3100 also includes a handheld portion 3130 at its proximal end for manual actuation and/or maneuverability such as in and out laparoscopic port 3300, and through it, in and out an internal body cavity if laparoscopic port 3300 is deployed in the body cavity wall. Tool introducer 3100 may be configured, such as sized and/or shaped, such that it can place tool 3200 in a certain predetermined position in laparoscopic port 3300 or at least in minimal distance to its distal end 3330. In some such embodiments, handheld portion 3130 may be shaped and/or sized such as it can serve as a stopper for maximal projection of tool 3200 in tubular body 3310 inner passage.

In some embodiments, tool introducer 3100 is configured such that, at locking, a tool connector 3220 of the tool 3200 projects towards tube opening at distal end 3330 and distanced with a distance P there from being at least 3 cm, or optionally by at least 5 cm, or optionally by at least 10 cm, or optionally by at least 20 cm, or higher, or lower, or any intermediate value.

Tool 3200 may be readily provided in locking means 3120 and it can be introducible thereto via proximal opening at proximal end 3340 with tool introducer 3100.

FIG. 9 schematically illustrates a cut view representing a tool introducer 4100 with a powered tool deployer 4400, in accordance with an exemplary embodiment of the present invention. Tool introducer 4100 is similar in many respects to tool introducer 3100 and is meant for introduction in an elongated tubular member, such as laparoscopic port 4300, and for positioning and/or locking a surgical tool such as tool 4200 thereinside, to a predetermined distance from a distal opening thereof being at least 3 cm in length. Tool introducer 4100 includes an elongated body comprising of a distal member 4120 with locking means adapted for selectively locking in tool 4200, which is rotationally connected with a hollow proximal member 4130 starting with a handheld portion 4110. At the intersection of distal member 4120 and proximal member 4130 there is a recess 4140 configured for interaction with a corresponding projecting portion 4462 of powered tool deployer 4400, optionally having non-circular cross section, either symmetrical (such as hexagonal cross section) or not symmetrical (such as a rectangular slit).

Powered tool deployer 4400 is configured to couple with tool introducer 4100 (when, optionally, placed in laparoscopic port 4300) and rotate distal member 4120 about proximal member 4130, thereby rotating tool 4200, such that when a distal end of a tool manipulator elongated shaft, having a fitting portion configured to thread to corresponding portion in tool 4200, is pressed thereto, then tool 4200 will connect to the tool manipulator, and vice versa. Powered tool deployer 4400 includes an elongated portion 4410 sized to fit and extend in the hollow proximal member 4130 of tool introducer 4100, and a proximal handheld part 4420 containing the powering components, such as motor 4440, controller 4450 and battery 4430. Alternatively and optionally, the powering element may be a spring that is tensioned manually, and that may be released by an actuator to activate the tool deployer. Elongated portion 4410 houses a driver shaft 4460 ending with projecting portion 4462. Driver shaft 4460 is connected to motor 4440 and controller 4450 is configured to determine timing for powering motor 4440 to revolve diver shaft 4460 and, optionally, other features (such as torque moment, velocity and others). Battery 4430 is optionally rechargeable. Motor 4440 operation may begin selectively upon operator's triggering (such as by pressing a trigger or a push button; not shown), or automatically, for example upon connection of tool 4200 with a corresponding fitting portion of a tool manipulator (not shown). Tool 4200 and manipulator fitting portion may include specific identification and compatibility means such that motor 4440 will not be ignited unless proper identification and/or compatibility are met.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A tool introducer configured for introduction of a surgical tool and connection of the surgical tool to an elongated shaft of a tool manipulator, the tool introducer comprising:

a straight tube having a tube proximal opening and a tube distal opening, the straight tube enclosing a tube lumen, and the tube distal opening being configured to receive the elongate shaft; and a docking portion configured to selectively lock or unlock the surgical tool to said straight tube from displacing axially and/or rotationally in said tube lumen, wherein said docking portion is configured such that, when locked, a tool connector of said surgical tool projects towards said tube distal opening and is distanced proximally from said tube distal opening by at least 3 cm, and said docking portion includes an inner surface extending at an angle a relative to a longitudinal axis of said straight tube for centering and guiding the elongated shaft to said tool connector to connect the tool connector.

2. The tool introducer according to claim 1, wherein said straight tube is sized and shaped for being introduced in a body cavity via a laparoscopic port.

3. The tool introducer according to claim 2, wherein said tool introducer comprises an enlarged portion sized and/or shaped for barricading by said laparoscopic port.

4. The tool introducer according to claim 1, wherein, when locked, said tool connector is distanced from said distal opening by at least 5 cm.

5. The tool introducer according to claim 1, further comprising visualization means.

6. The tool introducer according to claim 1, further comprising lighting means.

7. The tool introducer according to claim 1, further comprising a seal member provided in or proximal to said lumen for sealing gas flow therefrom from a distal environment to a proximal environment.

8. The tool introducer according to claim 2, wherein said straight tube is extendable through and from said laparoscopic port by at least 15 cm.

9. The tool introducer according to claim 1, wherein said docking portion is selectively introducible in said lumen and fixedly connectable to said straight tube.

10. The tool introducer according to claim 9, wherein said docking portion comprises at least two opposing teeth selectively movable from an inward position at said locking to an outward position at said unlocking.

11. The tool introducer according to claim 1, wherein said docking portion is normally locking.

12. The tool introducer according to claim 3, wherein said docking portion is manually operational with a button provided at or adjacent said enlarged portion.

13. The tool introducer according to claim 1, wherein said surgical tool is connectable with said tool connector to a fitting portion of a tool manipulator, and said fitting portion is located at a distal end of an elongated shaft.

14. The tool introducer according to claim 13, wherein said elongated shaft has a maximal diameter equal to or smaller than 3 mm.

15. The tool introducer according to claim 13, wherein said tool manipulator and/or elongated shaft are introducible into a body cavity via an entry point remote to tool introducer entry.

16. The tool introducer according to claim 15, wherein said entry point is maintained by a second laparoscopic port.

17. A system comprising:

a surgical tool having a tool connector;

an elongated tube comprising a tube proximal opening, a tube distal opening, a tube lumen extending between said tube proximal opening and said tube distal opening, and a seal provided in said tube lumen; and a tool holder configured to selectively lock or unlock the surgical tool from displacing axially and/or rotationally in said tube lumen, wherein said tool holder is configured such that, when locked, the tool connector projects towards said tube distal opening and is distanced proximally from said tube distal opening by at least 3 cm, and said tool holder includes an inner surface extending at an angle a relative to a longitudinal axis of said elongated tube for centering and guiding an elongated shaft of a tool manipulator to said tool connector of said surgical tool the tool connector, wherein said elongated tube is telescopically introducible at a port proximal end, through a port lumen and bypassing a seal mechanism of a laparoscopic port interconnecting a body cavity and an outer environment.

18. The system according to claim 17, wherein said tool holder comprises a holder distal opening, a sealed proximal end, and a holder lumen extending at least partially therebetween.

19. The system according to claim 17, wherein said elongated tube has a proximal segment and distal segment, and said proximal segment has a larger outer diameter than said distal segment.

20. The system according to claim 18, wherein said holder lumen is adapted to receive an end portion of a needle system when said needle entering said tube distal opening via a port distal opening.

* * * * *